United States Patent [19]

Braun et al.

[11] Patent Number: 4,701,597
[45] Date of Patent: Oct. 20, 1987

[54] PORTABLE CONTACT LENS DISINFECTING APPARATUS

[75] Inventors: Alan J. Braun; Lawrence M. Smith, both of Rochester; Kelvin H. Wildman, Webster, all of N.Y.

[73] Assignee: Bausch & Lomb Incorporated, Rochester, N.Y.

[21] Appl. No.: 895,402

[22] Filed: Aug. 11, 1986

[51] Int. Cl.⁴ .............................................. A61L 2/04
[52] U.S. Cl. .................................. 219/521; 219/386; 219/504; 219/439
[58] Field of Search ............... 219/385, 386, 521, 504, 219/505, 438, 439, 441

[56] References Cited

U.S. PATENT DOCUMENTS

| | | | |
|---|---|---|---|
| 4,307,289 | 12/1981 | Thomas | 219/521 |
| 4,341,948 | 7/1982 | Sundström | 219/386 |
| 4,388,521 | 6/1983 | Thomas | 219/521 |
| 4,492,854 | 1/1985 | Ryder | 219/439 |

Primary Examiner—E. A. Goldberg
Assistant Examiner—Teresa J. Walberg
Attorney, Agent, or Firm—John S. Norton

[57] ABSTRACT

Contact lens disinfecting apparatus is provided having first and second lens-holding chambers, an electrically conductive heat sink thermally coupled to said chambers, electrically energizable heater thermally and electrically coupled to the heat sink, a thermostat, a second heat sink coupled to the thermostat and a thermally and electrically conductive heat transfer member connected between the heater and the second heat sink.

12 Claims, 4 Drawing Figures

U.S. Patent  Oct. 20, 1987  4,701,597
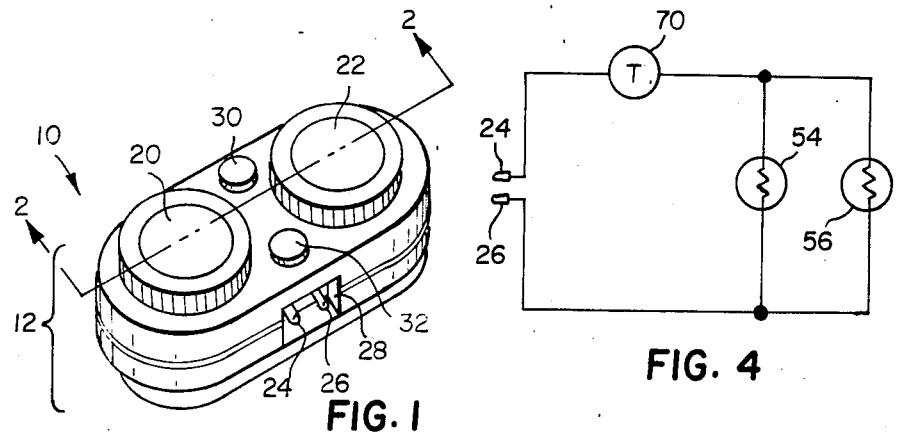
FIG. 1
FIG. 4
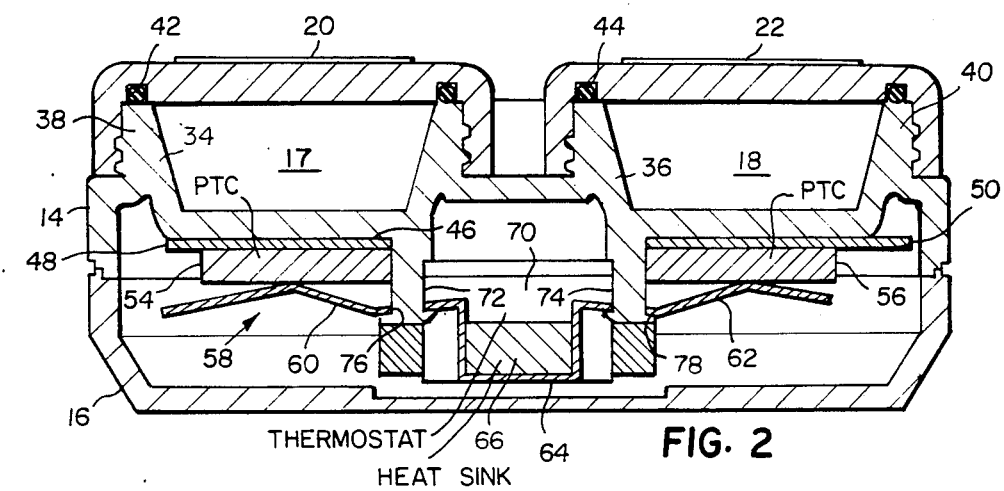
FIG. 2
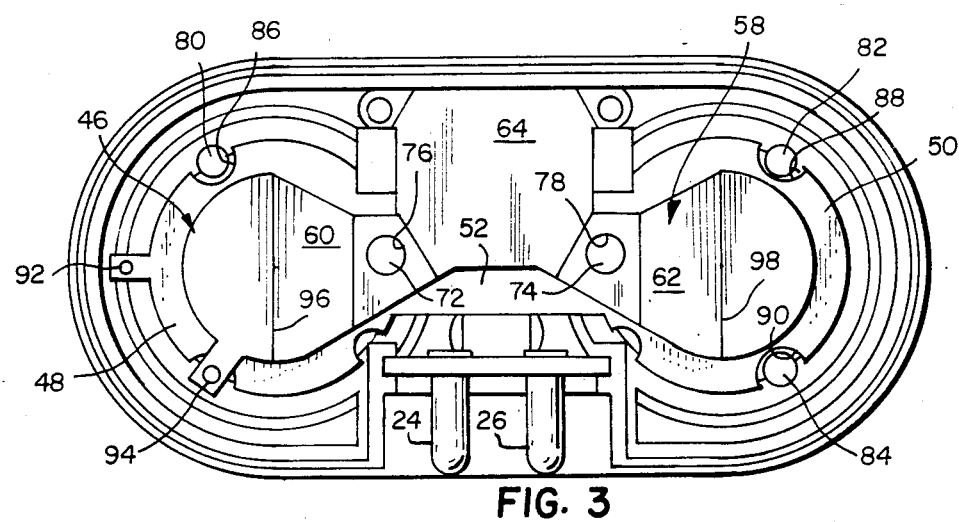
FIG. 3

PORTABLE CONTACT LENS DISINFECTING APPARATUS

BACKGROUND OF THE INVENTION

This invention relates in general to contact lens disinfecting apparatus and more particularly to a compact contact lens disinfecting and storage unit suitable for portable use.

The necessity for periodically disinfecting contact lenses and particularly soft contact lenses is well known. A variety of disinfectors is known in the art, including those shown in U.S. Pats. Nos. 3,998,590, 4,379,965, 4,472,623, 4,529,868 and 4,578,566, as well as other patents noted therein. Additional disinfectors are shown in French Patent Nos. 2,369,847 and 2,451,195.

Prior art disinfecting units are operated more slowly than is sometimes desirable. This is true as to those units that have heated the lenses within a separate carrying or storage case. Such an arrangement impedes the transfer of heat from the disinfector to the lenses. The one-piece disinfecting units have also disinfected more slowly than is desirable but for different reasons that will be discussed in detail infra. Lenses are ordinarily disinfected at night while the wearer sleeps and the length of the disinfecting cycle is of little importance. However, when disinfecting is forgotten and must be done in the morning, it is an advantage to be able to disinfect the lenses quickly. For example, the difference between a 45 minute disinfecting cycle and a 20 minute cycle is the difference between being able to complete the disinfecting cycle while showering or bathing and having to wait for the cycle to be concluded. A disinfecting unit capable of a short cycle time is very desirable.

Prior art disinfecting units have also been undesirably expensive. The manufacturing cost of a disinfecting unit is directly related to the number of parts comprising the unit the need for high precision parts and the difficulty of assembly. The reliability of a unit generally increases when the number of parts is reduced. There is a need for a reliable, low-cost short cycle time disinfecting unit.

The art has recognized that at minimum, a disinfector must include a lens holder, a heating device, a power source and either a thermostat time control, or manual means for disconnecting the heating device from the power source. Positive temperature coefficient (PTC) heaters have been advantageously employed as heaters. PTC heaters have the advantages of low cost, ease of use and high reliability. In order to most efficiently use a PTC heater as a heat source, it is desirable to interpose a heat sink between the heater and the chamber in which the lenses are placed. The heat sink reduces the rate at which the temperature of the PTC heater changes and reduces the likelihood that the PTC heater will develop hot spots that could damage the lenses. Heat sinks distribute heat to the chamber uniformly and allow more heat to be transferred from the PTC heater to the chamber in a given time than is possible by using a PTC heater alone. This is due in part to the characteristics of PTC heaters. Such heaters have a slight negative coefficient of resistance vs temperature below the transition temperature of the device. Above the transition temperature the resistance increases rapidly with increasing temperature. As the resistance of the device increases, the current flowing through the device decreases and the power consumption is reduced. By thermally coupling the PTC heater to a heat sink rather than directly to a lower thermal mass lens-holding well, the temperature increases more slowly and more power is converted to heat for increasing the temperature within the well. Even after the PTC heater transition temperature is reached and the heat output of the PTC heater is substantially reduced, the heat sink continues to transfer heat to the lens-holding chambers, maintaining the temperature within the chambers at a sufficient level to continue the disinfecting process.

A variety of types of heat sinks may be used. One known disinfecting unit includes a substantial volume of waxy material surrounding the PTC's and the lens-holding chambers. The heat necessary to convert the wax from a solid to a liquid is extracted from the PTC's during the heat up phase and is thereafter transferred from the wax to the lens-holding chambers even after power is removed from the PTC's. While this construction provides a disinfecting function, it is inefficient and slow. Much of the heat stored in the melted wax is wasted by radiation through the case rather than heating the lens-holding chambers. The time required to heat and cool the wax is longer than desirable.

SUMMARY OF THE INVENTION

Briefly stated and in accordance with a presently preferred embodiment of this invention, contact lens disinfecting apparatus is provided having first and second lens-holding chambers, an electrically conductive heat sink plate thermally coupled to said chambers, electrically energizable heating means thermally and electrically coupled to the heat sink, a thermostat, a second heat sink coupled to the thermostat and a thermally and electrically conductive heat transfer member connected between the heating means and the second heat sink.

While the aspects of the invention that are regarded as novel are described with particularity in the appended claims, the invention itself, together with further objects and advantages thereof, may be more readily appreciated by reference to the following detailed description thereof taken in conjunction with the accompanying drawings:

BRIEF DESCRIPTION OF THE DRAWINGS

FIG. 1 is a perspective view of a contact lens disinfecting unit in accordance with a presently preferred embodiment of this invention;

FIG. 2 is a section view thereof taken along line 2—2 of FIG. 1;

FIG. 3 is a bottom view thereof with the bottom cover removed showing the internal construction of the disinfecting unit; and FIG. 4 is a schematic diagram of a disinfecting unit according to the invention.

DESCRIPTION OF THE PREFERRED EMBODIMENT

Referring now to FIGS. 1 and 2, a contact lens disinfecting unit 10 is illustrated. Disinfector 10 has a generally rectangular two-part plastic body 12 having rounded ends and formed from upper and lower body portions 14 and 16 respectively. First and second round lens-holding chambers 17 and 18 are located in the upper portion of the body 12. Chambers 17 and 18 are closed by removable caps 20 and 22 respectively that preferably screw on and off. A pair of electrical contacts 24 and 26 are positioned in a recess 28 formed in lower body portion 16 for connecting the unit to a power source. A thermostat reset control button 30 protrudes through the top of disinfector 10 and an operating temperature indicator 32 is disposed adjacent to reset control button 30. Preferably, indicator 32 is an electrically energizable bulb, a thermally sensitive tape that changes color when heated, or other similar indicator.

FIG. 2 is a section view of the disinfecting unit of FIG. 1. The upper body portion 14 includes first and second lens-holding chambers 17 and 18 formed integrally therein and adapted to hold a quantity of solution together with the lens to be disinfected. The lens-holding chambers 17 and 18 are concave and designed for easy removal of the lenses therefrom. The chambers have generally cylindrical walls 34 and 36 respectively and each wall has an upwardly extending outside threaded barrel portion 38 and 40, respectively, onto which caps 20 and 22 may be threaded. Preferably sealing gaskets 42 and 44 are provided inside caps 20 and 22 respectively to prevent the solution from leaking if the disinfector is inverted.

A heat sink 46 is mounted adjacent the substantially flat underside of chambers 17 and 18 and is, preferably, closely thermally coupled thereto by layers of thermally conductive grease (not shown) between the heat sink and the underside of each chamber. While a single heat sink assembly 46 including two heat sink portions 48 and 50 and a connecting portion 52 is preferred, separate heat sinks, one for each lens-holding chamber, may be employed.

A pair of negative temperature coefficient electrical heaters 54 and 56, is provided, one positioned beneath the heat sink portion under each chamber. The heater 54 and 56 are also preferably coupled to the heat sink by layers of thermally conductive grease (not shown) between the heat sink and the heater.

The PTC heaters 54 and 56 and heat sink 46 are firmly held in position against the bottoms of chambers 17 and 18 by a clip 58 that functions as a combination spring clip, electrical contact, and heat transfer member. Clip 58 includes first and second outwardly extending retaining portions 60 and 62 that engage the undersides of PTC heaters 54 and 56, respectively. Clip 58 includes a generally U-shaped central portion 64 as best seen in FIG. 2.

One surface of a thermostat heat sink 66, as best shown in FIG. 2, contacts clip 58 at U-shaped portion 64. A manual reset thermostat 70 is disposed in engagement with the opposite surface of thermostat heat sink 66. Heat sink 46, heaters 54 and 56 and clip 58 are held in layered relationship against the underside of chambers 17 and 18 by swaged posts 72 and 74, that extend through holes 76 and 78 in clip 58. As best illustrated in FIG. 3, posts 80, 82 and 84 respectively engage cut outs 86, 88 and 90 in heat sink 48 to hold the heat sink in position during assembly of the unit.

A substantially rectangular electrical contact 92 is formed on one end of heat sink 46 and a similar contact 94 is formed on clip 58. Heat sink 46 and clip 58 make contact to the PTC heaters 54 and 56.

The electrical connections in the disinfecting unit are shown in schematic form in FIG. 4. PTC heaters 54 and 56 are connected in parallel and the combination is connected in series with thermostat 70 to electrical contacts 24 and 26. Electrical contact to PTC heaters 54 and 56 is made through contacts 92 and 94.

The thermal cycle of the disinfecting unit is designed to increase the temperature of the disinfecting liquid and lens within the lens-holding chamber rapidly to a predetermined level and to maintain the temperature for a time sufficient to adequately disinfect the lens. Applicants have discovered that merely connecting the PTC heaters and the thermostat to the same heat sink will not produce the desired results. The thermostat must be connected to the PTC heaters by a thermal structure that compensates for the thermal lag between the PTC heaters and the lens-holding chambers 17 and 18 that is created by the heat sink 46 and the chamber walls 34 and 36.

In accordance with this invention, clip 58 and heat sink 66 provide this compensating function. When power is supplied to the disinfecting unit, the thermostat 70 is initially closed and the PTC heaters 54 and 56 are energized during a first portion of the disinfecting cycle. Heat is transferred from the PTC heaters to heat sink 46 and from heat sink 46 to the lens-holding chambers 17 and 18. Simultaneously, heat is conducted by clip 58 from the PTC heaters to thermostat heat sink 66, and by thermostat heat sink 66 to thermostat 70. Because the thermal mass of heat sink 46 and the insulating properties of the walls 34, 36 of chambers 17 and 18, the temperature of the solution in chambers 17 and 18 lags the temperature of heat sink 46 which in turn lags the temperature of PTC heaters 54 and 56. When thermostat 70 reachers its designed cut off temperature, it disconnects the PTC heaters from the power source. Because heat is stored in heat sink 46, the temperature in the chambers 17 and 18 continues to increase afer power is removed from the PTC heaters 54 and 56. One possible method of control is to deenergize the PTC heaters 54 and 56 before the chambers 17 and 18 reach the desired temperature and allow them to coast up to the desired temperature. Direct thermal connection between the heaters 54 and 56 and the thermostat 70 will not be effective to do this under a range of ambient conditions. When ambient temperatures are high, the solution will reach a higher temperature than when ambient temperatures are low. Direct thermal connection between the thermostat 70 and heat sink 46 is also undesirable because it necessarily increases the size of the heat sink 46 by the area of the thermostat and makes the disinfecting unit larger and less efficient than desirable.

Accordingly, this invention simulates the thermal characteristics of the PTC heater-heatsink-chamber structure with a parallel thermal structure including the PTC heaters 54 and 56, clip 58, thermostat heat sink 66 and thermostat 70. The temperature of thermostat 70 lags the temperature of thermostat heat sink 66, which lags the temperature of clip 58, which lags the temperature of PTC heaters 54 and 56. Clip 58 and thermostat heat sink 66 cause the temperature of thermostat 70 to track the temperature of chambers 17 and 18 rather than the temperature of the PTC heaters 54 and 56. In this way, the thermostat 70 can accurately control the temperature in chambers 17 and 18 under a broad range of ambient temperature conditions for more effectively than could be accomplished by a direct connection to any of the elements in the main thermal path.

In accordance with this invention, heat sink 46 is selected to absorb a substantial amount of heat from heaters 54 and 56 and to transfer the heat to chambers 17 and 18. Clip 58 is preferably constructed from a thin resilient sheet of a material having a high thermal conductivity. Clip 58 is bent along lines 96 and 98 where the clip contacts heaters 54 and 56 so that a relatively small amount of heat is transferred from the heaters 54 and 56 to the clip 58. If clip 58 were connected directly to thermostat 70, the thermostat 70 would reach its cut-off temperature before the temperature in chambers 17 and 18 increased to a level where disinfection occurs. Accordingly, heat sink 66 is disposed between clip 58 and thermostat 70 to retard the increase in temperature in thermostat 70 so that it substantially tracks the temperature of lens-holding chambers 17 and 18.

Although the preferred embodiment of this invention contemplates a compact storage and disinfecting unit, the thermal techniques employed may be applied to a more conventional disinfector that uses a separate lens holding case adapted to be received in a heating chamber.

While the invention has been described in connection with a presently preferred embodiment thereof, those skilled in the art will recognize that certain modifications and changes may be made therein without departing from the true spirit and scope of the invention which accordingly, is intended to be defined solely by the appended claims.

We claim:

1. A thermostatically controlled heater comprising:
   a heating chamber;
   a heating element;
   an electrically conductive heat sink disposed between and electrically coupled to said heating element and said heating chamber;
   a thermostat for controlling said heating element;
   an electrically conductive thermostat heat sink coupled mechanically and electrically to said thermostat; and
   a heat transfer element connected between said heating element and said thermostat heat sink for transferring a controlled amount of heat from said heating element through said thermostat heat sink to said thermostat.

2. Contact lens disinfecting apparatus comprising:
   a heating chamber including a pair of lens holding cavities;
   heating means;
   a main heat sink coupling said heating means to said heating chamber, said main heat sink including a thermally conductive member having first and second heat sink portions disposed adjacent to, and thermally coupled to, said pair of lens holding cavities and a connecting portion connected between said heat sink portions;
   a thermostat;
   a thermostat heat sink coupled to said thermostat; and
   a heat transfer member connected between said heating means and said thermostat heat sink.

3. The disinfecting apparatus of claim 2 wherein said heating means comprises first and second heaters thermally coupled to said first and second heat sink portions, respectively.

4. The disinfecting apparatus of claim 3 wherein said first and second heaters comprise resistive heaters.

5. The disinfecting apparatus of claim 4 wherein said resistive heaters comprise positive temperature coefficient heaters.

6. Contact lens disinfecting apparatus, comprising:
   a heating chamber having first and second lens receiving chambers;
   a first electrically conductive heat sink thermally coupled to said chamber and including a thermally conductive member having first and second heat sink portions disposed adjacent to, and in thermal contact with, said first and second lens receiving chambers respectively and a connecting portion coupling said heat sink portions;
   electrically operable heating means thermally and electrically coupled to said heat sink;
   a thermostat;
   a second heat sink coupled to said thermostat; and
   a thermally and electrically conductive heat transfer member connected between said heating means and said second heat sink.

7. The disinfecting apparatus of claim 6 further comprising first and second electrical contacts, said first contact connected to said thermostat and said second contact connected to one of said first electrically conductive heat sink and said heat transfer member; and said thermostat electrically connected to the other of said first electrically conductive heat sink and said heat transfer member.

8. The disinfecting apparatus of claim 6 further comprising a housing having said lens receiving chambers formed therein and enclosing said first heat sink, said heating means, said thermostat, said second heat sink and said heat transfer member and including means for mechanically holding said first heat sink, said heating means and said heat transfer member is layered relationship adjacent said lens receiving chambers.

9. The disinfecting apparatus of claim 6 further comprising first and second positive temperature coefficient heaters disposed adjacent to, and thermally coupled to, said first and second heat sink portions, respectively.

10. The disinfecting apparatus of claim 9 wherein said conductive heat transfer member includes a thermally and electrically conductive spring member having first and second retaining portions engaging said positive temperature coefficient heaters respectively and biasing them into engagement with said first heat sink and biasing said first heat sink into engagement with said lens receiving chambers.

11. The disinfecting apparatus of claim 10 wherein said spring member further comprises a central portion thermally engaging said thermostat.

12. The disinfecting apparatus of claim 10 wherein said retaining portions of said spring member comprise first and second substantially flat portions joined at an angle along a fold line and wherein said retaining portions contact said positive temperature coefficient heaters along said fold lines.

* * * * *

UNITED STATES PATENT AND TRADEMARK OFFICE
CERTIFICATE OF CORRECTION

PATENT NO. : 4,701,597

DATED : October 20, 1987

INVENTOR(S) : Alan J. Braun et al

It is certified that error appears in the above—identified patent and that said Letters Patent is hereby corrected as shown below:

Col. 3, line 31, change "negative" to "positive".

Signed and Sealed this

Thirty-first Day of May, 1988

Attest:

DONALD J. QUIGG

Attesting Officer

Commissioner of Patents and Trademarks